United States Patent
Finmans et al.

(10) Patent No.: US 7,728,166 B2
(45) Date of Patent: Jun. 1, 2010

(54) PROCESS FOR THE PRODUCTION OF METAL SALTS OF TRIFLUOROMETHANE SULPHONIC ACID AND THEIR USE AS ESTERIFICATION CATALYSTS

(75) Inventors: Peter Finmans, Duisburg (DE); Detlef Hoell, Moers (DE); Hans-Jurgen Vossler, Rheinberg (DE); Martina Rozek, Kempen (DE); Michael James Green, Johannesburg (ZA); Rafael Roggenbuck, Gelsenkirchen (DE)

(73) Assignee: Sasol Solvents Germany GmbH, Hamburg (DE)

( * ) Notice: Subject to any disclaimer, the term of this patent is extended or adjusted under 35 U.S.C. 154(b) by 687 days.

(21) Appl. No.: 10/579,489

(22) PCT Filed: Nov. 18, 2004

(86) PCT No.: PCT/EP2004/013107

§ 371 (c)(1),
(2), (4) Date: May 11, 2007

(87) PCT Pub. No.: WO2005/049556

PCT Pub. Date: Jun. 2, 2005

(65) Prior Publication Data

US 2007/0255073 A1   Nov. 1, 2007

(30) Foreign Application Priority Data

Nov. 18, 2003  (DE) .............................. 103 53 934

(51) Int. Cl.
*C07C 69/66* (2006.01)
*C07C 309/06* (2006.01)

(52) U.S. Cl. ..................... 560/180; 560/179; 562/113

(58) Field of Classification Search .................. 562/113; 560/179, 180
See application file for complete search history.

(56) References Cited

U.S. PATENT DOCUMENTS

| 4,219,540 | A | | 8/1980 | Soldati et al. | |
| 6,111,136 | A | * | 8/2000 | Marzouk et al. | 562/113 |
| 6,479,698 | B1 | * | 11/2002 | Pevere et al. | 562/113 |

FOREIGN PATENT DOCUMENTS

| EP | 0287426 | 1/1988 |
| EP | 0945423 | 3/1999 |
| JP | 09227442 | 2/1997 |
| JP | 2003073330 | 12/2003 |

OTHER PUBLICATIONS

Houben-Weyl, Methoden der Organischen Chemie, Georg Thime Verlag, Stuttgarr Bd. VIII 4. edition, 1952, p. 520.

Ishihara et al., "Scandium Triflueromethansulfonate as an Extremely Active Lewis Acid Catalyst in Acylation of Alcohols with Acid Anhydrides and Mixed Anhydrides" Journal of Organic Chemistry, American Chemical Society, Easton, USA vol. 61, 1996, p. 4560-4567.

Schmeisser et al. "Zur Chemie der Perfluoralkansulfonsauren" Chemische Berichte, CVerlag Chemie GmbH, vol. 103, 1970, p. 868-879.

George A. Olah Boron, Aluminum and Gallium Tris(trifluoromethanesulfonate) (Triflate): Effective New Friedel-Crafts Catalysts, American Chemical Society, Washington, DC, USA vol. 110, No. 8, 1988, p. 2560-2565.

Atsushi Kawada, "Lanthanide Trifluoromethanesulfonates as Reusable Catalysts: Catalytic Fridel-Crafts Acylation" Journal of the Chemical Society, Chemical Communications, Chemical Society, Letchwood, GB, vol. 14, Jul. 21, 1993, p. 1157-1158.

* cited by examiner

*Primary Examiner*—Peter G O'Sullivan

(57) ABSTRACT

The subject matter of the invention is a process for the production of metal salts of trifluoromethane sulphonic acid by reacting trifluoromethane sulphonic acid with a metal alcoholate and the use thereof as esterification catalyst and/or transesterification catalyst for the production of hydroxycarboxylic acid esters.

26 Claims, No Drawings

PROCESS FOR THE PRODUCTION OF METAL SALTS OF TRIFLUOROMETHANE SULPHONIC ACID AND THEIR USE AS ESTERIFICATION CATALYSTS

BACKGROUND OF THE INVENTION

1. Field of the Invention

The invention relates to a process for the production of metal salts of trifluoromethane sulphonic acid by reacting trifluoromethane sulphonic acid with a metal alcoholate and their use as esterification catalyst and/or transesterification catalyst for the production of hydroxycarboxylic acid esters.

2. Description of Prior Art

Trifluoromethane sulphonic acid ($CF_3SO_3H$) is one of the strongest organic acids. Its protonation power is stronger than that of sulphuric acid. Its metal salts, i.e. metal perfluoromethane sulphonates, also called metal triflates, are available as solids or in solution.

The most frequent fields of application of metal compounds of trifluoromethane sulphonic acid are their use as catalyst in the polymerisation of aromatic alkenes, of aromatic monomers, in electrophilic polymerisation of 1,3-pentadiene, the cationic ring opening polymerisation of tetrahydrofuran, in the Michael reaction of O-silylated ketene acetals with alpha,beta-unsaturated esters. Further fields of application are aldol and Friedel-Crafts reactions.

From U.S. Pat. No. 4,219,540, the production of metal salts of trifluoromethane sulphonic acid and their use in antiperspirants is known. The aluminium salt of trifluoromethane sulphonic acid is produced by adding trifluoromethane sulphonic acid at room temperature to an aqueous suspension of barium carbonate and stirring the mixture, filtering it and removing water from it at reduced pressure and elevated temperature and drying it.

The barium trifluoromethane sulphonate thus obtained is again dissolved in water, stirred and aluminium sulphate dissolved in water is added at room temperature. After heating, filtration is carried out and the filtrate is decolorised with carbon, filtered once more and water is driven off at reduced pressure and elevated temperature, and it is dried. In a similar manner, the corresponding triflates have been produced for the rare earth metals Ce, La and the Nd—Pr alloy didymium [neodymium-praeseodymium-alloy].

A disadvantage is the complicated recovery of the metal triflate and the low yield with respect to the trifluoromethane sulphonic acid used.

SUMMARY OF THE INVENTION

In comparison with the process described above, the production process according to the invention leads, among other things, to the following improvements:
  simpler synthesis,
  high yields,
  no formation of salts as waste-producing products and
  higher purity with respect to foreign metal ions since no foreign metal compounds are used for the synthesis.

Thus, the following purities are independently of each other obtainable for the aluminium triflates/aluminium alcoholate triflates according to the invention
  for Na and Fe, less than 100 ppm respectively
  for Ba, Pb, Ni, Ti, Va and Zn, less than 10 ppm respectively
  for As, Co, Hg, Mn, Sb, Se, Sn and Ta, less than 1 ppm respectively

DESCRIPTION OF PREFERRED EMBODIMENTS

The object of the invention is achieved by way of a process for the production of metal salts of trifluoromethane sulphonic acid by reacting trifluoromethane sulphonic acid $CF_3SO_3H$ with a metal alcoholate, if necessary in a solubiliser/diluent at a temperature of −40° C. to +100° C., preferably 0° C. to 80° C., the metal (M) being Li, Na, K, Ba, Mg, Ca, Al, In, Sn, Sc, Y, La, Ti, Zr, Fe, Cu, Ag or Zn, preferably Al, Ti or Zr, and the alcoholate group(s) of the metal alcoholate exhibiting 1 to 28 carbon atoms, preferably 2 to 8 carbon atoms, based on one group, as well as, optionally, furthermore the following: hydroxy groups (C—OH), ether bonds (C—O—C) and/or more than one alcoholate bond (M—O—).

According to the invention, metal triflates (metal salts of trifluoromethane sulphonic acid) are compounds which exhibit at least one trifluoromethane sulphonic acid group.

Apart from at least one acid group, the metal triflate can also exhibit one alcoholate group with 1 or 2 bonds (2-dentate ligand) with the metal and additionally optionally ether groups and/or free hydroxy groups.

Preferably, the metal salt of trifluoromethane sulphonic acid has the following structure

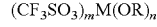

$$(CF_3SO_3)_m M(OR)_n$$

wherein
(m+n) in total correspond to the valency of the metal cation and m is at least 1, m preferably corresponding to the valency of the metal,
R is a hydrocarbon radical with 1 to 28, preferably 2 to 8, carbon atoms which optionally comprises 1 to 8 ether groups, in particular 1 to 3 ether groups and/or 1 to 4 hydroxy groups,
  is hydrogen, preferably, insofar at least one R is not hydrogen and R can be different for each n and
M is Li, Na, K, Ba, Mg, Ca, Al, In, Sn, Sc, Y, La, Ti, Zr, Fe, Cu, Ag or Zn, preferably Al, Ti or Zr.

According to the process of the invention, metal triflates of high purity can be produced in a surprisingly simple manner in the dissolved state or as solid pure substance by adding $CF_3SO_3H$ to metal alkoxides. Alcohol which is released is driven out after or during the addition of the trifluoromethane sulphonic acid.

The target substance can be removed from the reaction mixture by extraction with water. In contrast, the metal triflates exhibiting at least one alcohol group are frequently water insoluble in the case of a chain length of more than 4 of the carbon atoms of the alcohol group and can thus be separated from the water-soluble product and/or excess alcohol. Alcohol formed in the hydrolysis or alcohol used as diluent can be separated off by phase separation if water insoluble alcohols are involved (>=C4, preferably >=C5).

According to a further object of the invention, the metal triflates, as described above, among other things, can be used as catalysts for the synthesis of hydroxycarboxylic acid esters by conversion of hydroxycarboxylic acids with alcohols and/or transesterification.

Numerous routes for producing hydroxycarboxylic acid esters, in particular lactic acid esters, have been described. One variation is the direct esterification of hydroxycarboxylic acid with alcohols at elevated temperature without an addition of catalyst according to EP 0 287 426. In this case, the conversion is carried out at temperatures of 90 to 140° C. using alcohols with up to twelve carbon atoms for the preparation of optically active lactic acid esters. Since this process is merely quasi-continuous, the amount of equipment required is large.

Currently, proton-acidic or Lewis-acidic catalysts are used for the esterification process. These catalysts are frequently protonic acids such as hydrochloric acid, sulphuric acid, phosphoric acid, methane sulphonic acid, p-toluene sulphonic acid or acidic ion exchangers. Apart from the protonic acids, which frequently cause problems by corrosion, Lewis acids are also known as esterification catalysts, e.g. using metal halides or strongly acidic styrene resin in combination with the Lewis acid $AlCl_3$.

In the case of most esterification processes known from the state of the art, the water formed in the reaction is removed from the reaction mixture by azeotropic distillation by means of an entrainer. For this purpose, aliphatic and aromatic hydrocarbons are usually used.

Surprisingly enough, it has been found that hydroxycarboxylic acid esters can be obtained by the direct esterification of hydroxycarboxylic acids with alcohols in the presence of metal triflate catalysts which, moreover, exhibit an unusually high activity. The reaction times are short even when small quantities of catalysts are used. Depending on the alcohol used, the reaction times are usually 5 to 14 hours.

According to a further embodiment of the invention, the metal triflates, as described above, are used as catalysts for the transesterification of hydroxycarboxylic acid esters.

The metal triflates with at least one trifluoromethane sulphonic acid group are, in this case, brought into contact with hydroxycarboxylic acid esters, preferably with heating, with an alcohol and/or a further hydroxycarboxylic acid ester. As a rule, alcohols are used with a higher boiling point than the alcohol bound in the ester such that the alcohol with a lower boiling point is driven out of the reaction mixture. In this case, Li, Na, K, Ba, Mg, Ca, Al, In, Sn, Sc, Y, La, Ti, Zr, Fe, Cu, Ag or Zn, particularly preferably Al, Ti or Zr are preferably used as metal component of the metal triflates.

The alcohols and/or alcoholate groups used for the esterification and transesterification can be branched, straight chain, saturated, unsaturated, aromatic, primary, secondary or tertiary and exhibit preferably 1 to 28 carbon atoms and, if necessary, 1 to 8 ether groups or 1 to 5 further hydroxy groups. The reacted aliphatic and aromatic hydroxycarboxylic acid esters contain at least one hydroxy group (—OH) and one carboxylic acid ester group (—COO—) respectively.

The esterification and transesterification can be carried out at temperatures of 60 to 250° C. and pressures of 0.05 to 40 bar. The molar ratio of the alcohol used to the ester groups of the hydroxycarboxylic acid ester used is preferably 0.5 to 2.0 and the catalyst is preferably used in an amount of 0.02 to 1.0% by weight, based on the hydroxycarboxylic acid ester to be reacted.

The work-up of the hydroxycarboxylic acid ester produced by transesterification can take place by distillation at temperatures in the region of 60° C. to 250° C. and pressures of 1 hPa to 1013 hPa or by stripping with steam at temperatures of 120° C. to 200° C. and pressures of 1 hPa to 1013 hPa, it being possible for the work-up to take place either directly from the raw product or after removing the catalyst and filtering the raw product. In the case of a work-up by distillation, the catalyst can be removed by adsorption with activated carbon, aluminium hydroxide or aluminosilicate before distillation or remain in the bottom product and be recycled into the process.

Catalysts which are used in the esterification reactions can also be used as catalysts for transesterifications.

The metal triflates are easy to handle and without problems both in the pure form and in solution. The compounds are stable and pose no particular requirements regarding storage. During handling, the usual measures for handling irritant substances need to be complied with. High yields of hydroxycarboxylic acid esters are achieved with a simultaneously high selectivity, the usual by-products such as the oligo and poly(hydroxycarboxylic acid) esters formed by the reaction of hydroxycarboxylic acids with each other, being formed in much lower proportions compared with the use of conventional catalysts. Moreover, they can be recycled into the reaction in order to be reesterified with an excess of alcohol to form simple hydroxycarboxylic acid esters.

A great advantage of the metal triflates compared with the protonic acids as catalyst is the low tendency to corrosion. It is by a factor of >10 lower than that of a reaction mixture with the same proportion of sulphuric acid as catalyst.

The metal triflates can be produced in a simple manner as solids or in solution by reacting the acid with a metal alcoholate, as described above. In this respect, it is particularly advantageous that reaction products which have not been purified and contain e.g. suitable alcohols can also be used directly in the esterification reaction.

However, other processes are also known according to which aluminium salts or rare earth metal salts of trifluoromethane sulphonates are available, e.g. from the corresponding metal carbonates according to U.S. Pat. No. 4,219, 540 already cited above.

The metal triflates have a high Lewis acid activity and are stable in aqueous media. They can therefore be considered for use for numerous organic reactions in which water is contained in the starting materials, is formed as reaction product or used as solvent and/or in micro-emulsions. Thus, the metal triflates according to the invention are generally suitable in particular for reactions in protic media.

Hydroxycarboxylic acids according to the meaning of this invention are hydroxycarboxylic acids which contain at least one alcohol function (—OH) and one carboxylic acid function (COOH, including COO).

For the present invention, the following hydroxycarboxylic acids, are suitable in particular as compounds obtained from raw materials both for the esterification reaction and the transesterification reaction: glycolic acid, lactic acid, β-hydroxy propionic acid, α-hydroxybutyric acid, β-hydroxybutyric acid and γ-hydroxybutyric acid, malic acid, tartaric acid, citric acid, mandelic acid and salicylic acid.

These hydroxycarboxylic acids are reacted with primary, secondary and tertiary, straight chain and branched alcohols with a chain length of 1 of 28 carbon atoms. Metal salts of trifluoromethane sulphonic acid (triflates) are used as catalysts. The following are used as metals: Li, Na, K, Ba, Mg, Ca, Al, In, Sn, Sc, Y, La, Ti, Zr, Fe, Cu, Ag and Zn.

The hydroxycarboxylic acid esters of the above-mentioned acids have a variety of applications. The esters of lactic acid with ethanol and n-butanol (ethyl lactate and n-butyl lactate) are used, among other things, as environment-friendly additives in solvent formulations for paints and in purifier formulations for the semiconductor industry. In this case, they are used for removing photo resists from templates, for example. In addition, both esters have been approved by the FDA as additives in the food industry. The esters of other alcohols with a higher number of carbon atoms are also used in these fields or in the cosmetics industry. Cetyl lactate, in particular, is used in the U.S.A. in a large number of cosmetic formulations. The esters of citric acid with alcohols and alcohol mixtures, in particular with 4 to 16 carbon atoms, are used mainly as plasticisers for polymers. The esters of other hydroxycarboxylic acids have potentially the same fields of application.

EXAMPLE

A Production of Metal Triflates

The experiments were carried out in a 1000 ml reaction flask of glass equipped with a thermometer, a distillation attachment, dropping funnel and stirrer as well as a vacuum distillation device with cooling traps.

To remove the heat of reaction the reaction vessel was cooled by means of an ice bath.

Example A1

Production of Aluminium Tristrifluoromethane Sulphonate in Isotridecanol 21.44 g of aluminium triisopropylate and 193.86 g of isotridecanol were introduced into a reaction flask and 45.02 g of trifluoromethane sulphonic acid were metered in at room temperature (25° C.) with vigorous stirring within approximately 1 h by means of a dropping funnel.

The reaction vessel was cooled continuously such that the bottom temperature did not exceed 40° C.

Subsequently, a vacuum of 100 mbar was applied and the product heated to 110° C. within approximately 45 minutes.

At the same time, the pressure was reduced to 50 mbar and the co-product isopropanol was removed by distillation. Aluminium tristrifluoromethane sulphonate $(CF_3SO_3)_3Al$ remained in the flask in solution.

Example A2

Production of Aluminium Tristrifluoromethane Sulphonate in Isopropanol 10.72 g of aluminium triisopropylate and 87.93 g of isopropanol were introduced into the reaction flask and 22.5 g of trifluoromethane sulphonic acid were metered in at room temperature (25° C.) with vigorous stirring within 1 h by means of a dropping funnel. The reaction vessel was cooled continuously such that the bottom temperature did not exceed 40° C. Subsequently, the reaction mixture was stirred for 1 h at room temperature. Aluminium tristrifluoromethane sulphonate $Al(CF_3SO_3)_3$ in isopropanol remained in the flask.

Example A3

Production of Zirconium Tetrakistrifluoromethane Sulphonate in Isotridecanol 40.2 g of zirconium tetra-n-butylate and 305.08 g of isotridecanol were introduced into the reaction flask, 60.03 g trifluoromethane sulphonic acid were metered in at room temperature (25° C.) with vigorous stirring within 1 h by means of a dropping funnel. The reaction vessel was cooled continuously such that the bottom temperature did not exceed 40° C. Subsequently, the product was heated under vacuum of 100 mbar to 110° C. within 45 minutes. At the same time, the pressure was reduced to 50 mbar and the co-product n-butanol was removed by distillation. Zirconium tetrakistrifluoromethane sulphonate $Zr(CF_3SO_3)_4$ remained in the flask in solution.

Example A4

Production of Aluminium Tristrifluoromethane Sulphonate, Solvent Free 21.4 g of aluminium triisopropylate and 64.4 g of xylene were introduced into the reaction flask and heated in a rotary evaporator under a vacuum of 500 mbar to 70° C. 45.0 g of trifluoromethane sulphonic acid were added within 60 min. and xylene and the co-product isopropanol were drawn off at 98° C. and 400 mbar.

Aluminium tristrifluoromethane sulphonate $Al(CF_3SO_3)_3$ remained in the flask as a solid. By means of AAS, metal impurities were determined which were below the limit values indicated in the introduction to the description.

B Production of Hydroxycarboxylic Acid Using Metal Triflate Catalysis

Production of Lactic Acid Esters (Lactates)

In the following, it is described how hydroxycarboxylic acids can be obtained be the direct conversion of hydroxycarboxylic acids with alcohols using metal triflates as catalysts. In this process, either the alcohol or the acid was used in excess (up to 100%).

The water formed in the reaction was removed from the reaction mixture by azeotropic distillation using an entrainer. Aliphatic and aromatic hydrocarbons or dialkyl ethers were used as entrainers.

The reactions for the production of the lactic acid esters were carried out in a 2l glass flask equipped with a column (Sulzer packing of stainless steel), a capillary for the introduction of nitrogen, a dropping funnel and a PT100 heat sensor. At the top of the column was a water separator with a reflux condenser. A heating dome was used for heating. The reaction conditions employed were within a temperature range of 40 to 180° C. and a pressure range of 0.2 to 10 bar, depending on the alcohol used.

Example B1

Production of Lactic Acid Ethyl Ester 563.0 g of lactic acid (80% by weight in water, i.e. based on lactic acid and used as an 80% by weight solution in water), 460.7 g of ethanol and 2.3 g $Al(OTf)_3$ (in 9 g of isotridecanol, based on $Al(OTf)_3$ and used as a 20% by weight solution in isotridecanol), were introduced into a reaction flask. The water separator was filled with diisopropyl ether which served as entrainer. A further 300 g of diisopropyl ether were introduced into the flask. The bottom was heated to 80 to 90° C. such that a good reflux was formed and forming water was removed azeotropically at a head temperature of 62° C. The course of the reaction was monitored by way of the acid number. The esterification was carried out up to an acid number of <2 mg KOH/g. This was reached after 12 h, whereby a conversion of more than 99% had been reached for the hydroxycarboxylic acid.

The yield of ethyl lactate was more than 88%. The di-lactic acid ethyl ester was formed in a yield of 11%.

The crude product was neutralised with $Ca(OH)_2$ to remove the residual acid and the catalyst and filtered. The entrainer and excess alcohol were removed by distillation from the filtrate and the crude product was subjected to fractional distillation at reduced pressure.

Example B2

Production of Lactic Acid Ethyl Ester 563.0 g of lactic acid (80% by weight in water) were introduced into a reaction flask and part of the water was removed at reduced pressure at elevated temperature within 30 min such that the lactic acid was present as an approximately 95% solution. 460.7 g of ethanol and 2.3 g of Al(OTf)$_3$ (in 9 g of isotridecanol) were added.

The water separator was filled with diisopropyl ether which served as entrainer. A further 300 g of diisopropyl ether were introduced into the flask and the bottom was heated to 80 to 90° C. such that a good reflux was formed and the water generated was removed azeotropically at a head temperature of 62° C. The course of the reaction was monitored by way of the acid number.

The esterification was carried out up to an acid number of less than 2 mg KOH/g. This, including drying of the lactic acid, was achieved after 9.5 h. The conversion of lactic acid was more than 99%. The yield of ethyl lactate was more than 87%, the dilactic acid ethyl ester was formed in a 12% yield. The work-up of the crude product was carried our in a manner analogous to example B1.

Example B3

Production of Lactic Acid Butyl Ester 563.0 g of lactic acid, based on lactic acid and used as an 80% by weight solution in water, 741.2 g of n-butanol and 2.3 g of Al(OTf)$_3$ (in 9 g isotridecanol) were introduced into the reaction flask. The water separator was filled with diisopropyl ether which served as entrainer. A further 300 g of diisopropyl ether were introduced into the flask. Bottom was heated to 90 to 120° C. such that a good reflux was formed and the water generated was removed azeotropically at a head temperature of 66° C. The course of the reaction was monitored by way of the acid number and the esterification was carried out up to an acid number of less than 2 mg KOH/g. This was reached after 6 h whereby a conversion of more than 99% was reached for the hydroxycarboxylic acid. The yield of ethyl lactate was more than 95%, the dilactic butyl ester was formed in a yield of approximately 4%. The work up of the crude product was carried out in a manner analogous to example B1.

Production of Citric Acid Esters (Citrate)

The reaction for the production of citric acid esters was carried out in a 21 glass flask equipped with a column (Raschig rings of stainless steel), a capillary for the introduction of nitrogen, a dropping funnel and a PT100 heat sensor. A water separator with a reflux condenser was fitted to the head of the column. A heating dome was used for heating. The reaction temperature was in the range of 80 to 180° C. and a pressure range of 0.2 to 2 bar.

Example B4

Production of a Citric Acid Ester with a Mixture of Linear C6/C8 Alcohols, Catalyst Al(OTf)$_3$ 384.2 g of citric acid, 1048.4 g of C6/C8 alcohol and 1.2 g of Al(OTf)$_3$ (in 4.5 g of isotridecanol) were introduced into a reaction flask. The alcohol served simultaneously as entrainer for the water. The bottom was heated to 110° C. at reduced pressure such that a good reflux was formed and the water generated was removed azeotropically at a head temperature of 80° C.

The course of the reaction was monitored by way of the acid number and esterification was carried out up to an acid number of 0.6 KOH/g which was reached after 9 h.

The conversion of citric acid was thus greater than 99%. The reaction mixture was dissolved with an equimolar quantity of NaOH, based on the acid number, neutralised in 1% water (based on the amount weighed in) for 20 min at 40° C. and subsequently dried for 15 to 20 min at reduced pressure and temperature of up to 80° C. To remove the excess alcohol, the crude product was stripped in a laboratory stripping apparatus using steam at 135 to 195° C.

Example B5

Production of a Citric Acid Ester with a Mixture of Linear C6/C8 Alcohols, Catalyst, Zr(OTf)$_4$ 864.5 g of citric acid, 2358.8 g of C6/C8 alcohol and 1.3 g of Zr(OTf)$_4$ (in 5.1 g of isotridecanol) were introduced into a reaction flask. The alcohol served simultaneously as entrainer. The bottom was heated to 110° C. at reduced pressure such that a good reflux was formed and the water generated was removed azeotropically at a head temperature of 80° C. The course of the reaction was monitored via the acid number and continued up to an acid number of 0.6 mg KOH/g which was reached after 14 h. The conversion of citric acid was thus more than 99%. The work-up was carried out in a manner analogous to example B4.

Example B6

Production of a Citric Acid Ester with a Mixture of Linear C6/C8 Alcohols, Catalyst, Sn(OTf)$_2$ 384.2 g of citric acid, 1048.4 g of C6/C8 alcohol and 0.1 g of Sn(OTf)$_2$ (in 0.4 g of isotridecanol) were introduced into a reaction flask. The alcohol served simultaneously as entrainer. The bottom was heated to 135° C. at reduced pressure such that a good reflux was formed and the water generated was removed azeotropically at a head temperature of 100° C. The course of the reaction was monitored via the acid number and continued up to an acid number of 0.5 mg KOH/g which was reached after 5 h. The conversion of citric acid was thus >99%. The work-up was carried out in a manner analogous to example B4.

The apparatus for the production of the tartaric ester and malic acid ester corresponded to that used for the production of citric acid ester.

Example B7

Production of Tartaric Acid Dialky Ester with C6/C8 Alcohol 450.3 g of tartaric acid, 1084.5 g of C6/C8 alcohol and 1.8 g of Al(OTf)$_3$ (in 7.2 g of isotridecanol) were introduced into the flask. The water separator was filled with cyclohexane which served as entrainer.

Further cyclohexane was introduced into the flask. The bottom was heated to 80 to 120° C. at reduced pressure and the water generated was removed azeotropically. The course of the reaction was monitored by way of the acid number and continued up to an acid number of <1 mg of KOH/g which was reached after 8 to 10 h, corresponding to a conversion of 99% with respect to the hydroxycarboxylic acid. The work up was carried out in a manner analogous to example B4.

Example B8

Production of Malic Acid Dialkyl Ester with C6/C8 Alcohol 402.3 g of malic acid, 1084.5 g of C6/C8 alcohol and 1.6 g of Al(OTf)$_3$ (in 6.4 g of isotridecanol) were introduced into a reaction flask. The water separator was filled with cyclohexane which served as entrainer. Further cyclohexane was introduced into the flask and the bottom was heated to 80 to 120° C. at reduced pressure and the water generated was removed azeotropically. The course of the reaction was monitored by means of the acid number and esterification was carried out up to an acid number of less than 1 mg of KOH/g. This was reached after 8 to 10 h as a result of which a conversion of more than 99% was reached for the hydroxycarboxylic acid. The work up took place in a manner analogous to example B4.

Transesterification of Lactic Acid Esters (Lactates)

In the following examples, conversions are described according to which hydroxycarboxylic acid esters are reesterified in the presence of metal triflates as catalysts and alcohols. In this process, the alcohol is used in excess (up to 100 mole %). The lower boiling alcohol liberated in the reaction is removed from the reaction mixture by distillation.

The reactions for the transesterification of lactic acid esters were carried out in a 1 l glass flask equipped with a column (filled with 6 mm Raschig rings) and a column head, a capillary for the introduction of nitrogen and a PT100 heat sensor. A heating dome was used for heating. The reaction conditions used were in a temperature range of 60 to 240° C. and a pressure range of 0.05 to 10 bar.

Example C1

Transesterification of Lactic Acid Ethyl Ester with N-butanol and Al(OTf)$_3$ 118.1 g (1.0 mole) of ethyl lactate and 148.2 g (2.0 mole) of n-butanol were introduced into the flask and 0.6 g (2.5 mmole) of Al(OTf)$_3$ were added as a 20% solution in n-butanol. The reaction mixture was heated to approximately 120° C. The ethanol formed in the reaction was withdrawn overhead. In the course of the reaction, the bottom temperature was raised stepwise up to approximately 140° C.

The increase in the head temperature from the boiling point of pure ethanol to the boiling point of pure n-butanol indicated the end of the reaction. The course of the reaction was additionally monitored by GC. For the work-up of the crude product, the catalyst was removed by means of an adsorption agent and the crude product was filtered.

Subsequently, a distillative separation of the excess alcohol and fractional distillation of the reaction product were carried out.

|  | Time (h) | | | |
| --- | --- | --- | --- | --- |
|  | 1.5 | 3.0 | 4.5 | 6.0 |
| Conversion of ethyl lactate (%) | 75.8 | 97.1 | 99.8 | 99.9 |
| Yield of n-butyl lactate (%) | 70.9 | 89.9 | 90.8 | 89.5 |
| Yield of oligomeric esters (%) | 4.9 | 7.2 | 9.0 | 10.4 |
| Selectivity % | 93.5 | 92.6 | 91.0 | 89.5 |

Example C2

Transesterification of Lactic Acid Ethyl Ester with N-Butanol and Zr(OTf)$_4$ 118.1 g (1.0 mole) of ethyl lactate and 148.2 g (2.0 mole) of n-butanol were introduced into the flask and 0.6 g (1.8 mmole) of Zr(OTf)$_4$ were added as a 20% solution in n-butanol. The reaction mixture was heated to approximately 120° C. The ethanol formed in the reaction was withdrawn overhead. In the course of the reaction, the bottom temperature was raised stepwise up to approximately 140° C.

The increase in the head temperature from the boiling point of pure ethanol to the boiling point of pure n-butanol indicated the end of the reaction. The course of the reaction was additionally monitored by GC.

|  | Time (h) | | | |
| --- | --- | --- | --- | --- |
|  | 1.0 | 2.0 | 3.0 | 6.0 |
| Conversion of ethyl lactate (%) | 50.9 | 78.4 | 93.5 | 99.6 |
| Yield of n-butyl lactate (%) | 46.6 | 73.6 | 87.7 | 90.4 |
| Yield of oligomeric esters (%) | 4.3 | 4.8 | 5.8 | 9.2 |
| Selectivity % | 91.6 | 93.8 | 93.8 | 90.8 |

Example C3

Transesterification of Lactic Acid Ethyl Ester with Isopropanol Al(OTf)$_3$ 118.1 g (1.0 mole) of ethyl lactate and 120.2 g (2.0 mole) of isopropanol were introduced into the flask and 0.6 g (2.5 mmole) of Al(OTf)$_3$ were added in the form of a 20% solution in isopropanol. The reaction mixture was heated to approximately 90° C. The ethanol formed in the reaction was withdrawn overhead. In the course of the reaction, the bottom temperature was raised stepwise up to approximately 105° C. After 6½ hours, the conversion of ethyl lactate was approximately 25%. This lower rate of reaction is attributable above all to the lower reaction temperature and the difficult distillative separation of the ethanol as a result of the slight difference in the boiling point with respect to isopropanol.

Example C4

Transesterification of Lactic Acid Isopropyl Ester with N-Butanol and Al(OTf)$_3$ 132.2 g (1.0 mole) of isopropyl lactate and 148.2 g (2.0 mole) of n-butanol were introduced into the flask and 0.66 g (2.8 mmole) of Al(OTf)$_3$ were added as a 20% solution in n-butanol. The reaction mixture was heated to approximately 125° C. The isopropanol formed in the reaction was withdrawn overhead. In the course of the reaction, the bottom temperature was raised stepwise up to approximately 145° C. The increase in the head temperature from the boiling point of pure isopropanol to the boiling point of the pure n-butanol indicates the end of the reaction. The course of the reaction was additionally monitored by GC.

Example C5

Transesterification of Citric Acid Tri-n-Butyl Ester with 1-Hexanol and Zr(OTf)₄

360.5 g of citric acid tri-n-butyl ester, 625.1 g of 1-hexanol and 1.8 g of Al(OTf)₃ (20% in isotridecanol) were introduced into the flask. The reaction mixture was heated to approximately 150° C. The n-butanol formed in the reaction was withdrawn overhead. The bottom temperature was increased stepwise in the course of the reaction to as much as approximately 180° C. To remove the excess alcohol, the crude product was stripped in a laboratory stripping device using steam at 135 to 195° C.

Example C6

Transesterification of Diisopropyl Tartrate with 1-Hexanol and AL(OTf)₃

234.3 g (1.0 mole) of diisopropyl tartrate (416.8 g of 1-hexanol (4.0 mole) and 1.17 g of Al(OTf)₃ (20% in isotridecanol) were introduced into the flask. The reaction mixture was heated to approximately 100° C. The i-propanol formed in the reaction was withdrawn overhead. The bottom temperature was increased stepwise in the course of the reaction to as much as approximately 120° C. To remove the excess alcohol, the crude product was stripped in a laboratory stripping device using steam at 135 to 195° C.

The invention claimed is:

1. Process for the production of metal salts of trifluoromethane sulphonic acid comprising at least one trifluoromethane sulphonic acid group comprising reacting trifluoromethane sulphonic acid (CF₃SO₃H) with a metal alcoholate, at a temperature of –40° C. to +100° C., the metal being selected from the group consisting of Li, Na, K, Ba, Mg, Ca, Al, In, Sn, Sc, Y, La, Ti, Zr, Fe, Cu, Ag, Zn and mixtures thereof and the alcoholate group(s) of the metal alcoholate comprising independent of each other 1 to 28 carbon atoms as well as optionally hydroxy groups (—OH), ether bonds (C—O—C) and/or more than one alcoholate bond (M—O—).

2. Process according to claim 1 characterised in that the metal salt of the trifluoromethane sulphonic acid is

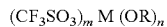

wherein
the sum of (m+n) corresponds to the valency of the metal cation and m is at least 1,
R is a hydrocarbon moiety with 1 to 6 carbon atoms and, optionally ether bonds (C—O—C) or is hydrogen and R can be different for each n and
M is Al.

3. A method for producing hydroxycarboxylic acid esters comprising reacting one or more hydroxycarboxylic acids with one or more alcohols in the presence of a metal salt of a trifluoromethane sulphonic acid exhibiting at least one trifluoromethane sulphonic acid group wherein the metal salts of the trifluoromethane sulphonic acid comprise Mg, Ca, Al, Sn, Ti, Zr, Fe, Cu or Zn as metal.

4. The method of claim 3 characterised in that the metal of the metal salts of the trifluoromethane sulphonic acid comprises MgrZn Al, Ti or Zr as metal.

5. The method of any one of claims 3 or 4 characterised in that the alcohols exhibit 1 to 28 carbon atoms and, optionally furthermore 1 to 8 ether groups and/or further 1 to 5 hydroxy groups.

6. The method of any one of claims 3 or 4 characterised in that the esterification is carried out at temperatures of 60 to 250° C. and, independently thereof, at pressures of 0.2 to 10 bar.

7. The method of any one of claims 3 or 4 characterised in that the esterification is carried out in the presence of an entrainer and water is removed by azeotropic distillation, the entrainer being preferably an aliphatic hydrocarbon, an aromatic hydrocarbon, a dialkyl ether or an alcohol, preferably the alcohol used for the esterification itself and/or its/their mixture.

8. The method of any one of claims 3 or 4 characterised in that the molar ratio of the alcohol used to the carbonyl groups of the hydroxycarboxylic acid used is from 1:0.5 to 4.0, preferably 1.0 to 2.0.

9. The method of any one of claims 3 or 4 characterised in that the catalyst is used in a quantity of 0.05 to 1.0 % by weight, based on the hydroxycarboxylic acid used.

10. The method of any one of claims 3 or 4 characterised in that the esterification is terminated by treating the crude product with metal alcoholates, alkali hydroxides or alkaline earth hydroxides and subsequently worked up by distillation.

11. A method of producing a hydroxycarboxylic acid ester comprising transesterification of a hydroxycarboxylic acid ester with at least one hydroxy group and at least one carboxylic acid ester group (—COO—), optionally having free carboxylic acid groups,
with an alcohol and/or another ester, in the presence of a catalyst comprising a metal salt of trifluoromethane sulphonic acid having at least one trifluoromethane sulphonic acid group
whereby at least one alcohol is removed from the reaction mixture and; wherein the metal of the salts of the trifluoromethane sulphonic acid comprise Mg, Ca, Al, Sn, Ti, Zr, Fe, Cu or Zn-as-metal.

12. The method of claim 11 characterised in that the metal salts of trifluoromethane sulphonic acid comprises Al.

13. The method of any one of claims 11 or 12 characterised in that the alcohols used comprise 1 to 28 carbon atoms and, optionally 1 to 8 ether groups and/or further 1 to 5 hydroxy groups.

14. The method of any one of claims 11 or 12 characterised in that the transesterification is carried out at temperatures of 60 to 250° C. and, independently thereof, at pressures of 0.05 to 10 bar.

15. The method of any one of claims 11 or 12 characterised in that the molar ratio of the alcohol employed relative to the ester groups of the hydroxycarboxylic acid ester to be converted is from 0.5 to 2.0.

16. The method of any one of claims 11 or 12 characterised in that the catalyst is used in a quantity of 0.02 to 1.0 % by weight, based on the hydroxycarboxylic acid ester to be converted.

17. The method of any one of claims 3 or 11 characterised in that the work-up of the hydroxycarboxylic acid ester takes place by distillation at temperatures in the range of 60° C. to 250° C. and pressures of 1 hPa to 1013 hPa or by stripping with a water vapour steam at temperatures of 120° C. to 200° C. and pressures of 1 hPa to 1013 hPa, in particular directly from the crude product or after removal of the catalyst and filtration of the crude product.

18. The method of claim 17 characterised in that the distillative work-up takes place after prior removal of the catalyst with activated carbon, aluminium hydroxide or aluminosilicate.

19. The method of any one of claims 3 or 11 wherein the metal salts of trifluoromethane sulphonic acid are used in the presence of water.

20. The method of claim 19 wherein the metal salts of trifluoromethane sulphonic acid are used in an aqueous environment comprising water, in particular as solvent or diluent, in addition to any water being formed in the course of the reaction.

21. The method of claim 1 wherein said metal is Al.

22. The process of claim 1 wherein said metal is Zr.

23. The process of claim 1 wherein said metal is Ti.

24. Process according to any one of claims 1, 2, 21, 22 or 23 characterised in that the reaction is conducted in the presence of a solvent selected from the group consisting of alcohols, aliphatic hydrocarbon, aromatic hydrocarbon, ethers having 2 to 32 carbon atoms, ketones having 2 to 32 carbon atoms, water and mixtures thereof.

25. Process according to any one of claims 1, 2, 21, 22 or 23 characterised in that the trifluoromethane sulphonic acid, optionally distributed with a solvent, is added to the metal alcoholate, optionally diluted with a solvent.

26. Process according to any one of claims 1, 2, 21, 22 or 23 characterised in that the metal alcoholate, optionally diluted with a solvent, is added to the trifluoromethane sulphonic acid, optionally diluted with a solvent.

* * * * *

UNITED STATES PATENT AND TRADEMARK OFFICE
CERTIFICATE OF CORRECTION

| | | |
|---|---|---|
| PATENT NO. | : 7,728,166 B2 | Page 1 of 1 |
| APPLICATION NO. | : 10/579489 | |
| DATED | : June 1, 2010 | |
| INVENTOR(S) | : Finmans et al. | |

It is certified that error appears in the above-identified patent and that said Letters Patent is hereby corrected as shown below:

Column 14, line 7, delete "distributed" and insert -- diluted --.

Signed and Sealed this

Thirtieth Day of November, 2010

David J. Kappos
*Director of the United States Patent and Trademark Office*